(12) United States Patent
Sabacinski et al.

(10) Patent No.: US 6,186,988 B1
(45) Date of Patent: Feb. 13, 2001

(54) WOUND IRRIGATION SYSTEM

(76) Inventors: Kenneth A Sabacinski, 3807 Bimini Ave., Cooper City; Donald Netinho, Jr., 644 NW. 155 Ter., Pembroke Pines, both of FL (US) 33026

( * ) Notice: Under 35 U.S.C. 154(b), the term of this patent shall be extended for 0 days.

(21) Appl. No.: 09/286,073

(22) Filed: Apr. 5, 1999

(51) Int. Cl.[7] ............................. A61M 35/00; B01F 5/04
(52) U.S. Cl. ......................... 604/289; 239/318; 137/893
(58) Field of Search .................. 604/289, 290, 604/293; 239/312, 311, 318, 428.5; 137/892, 893, 216

(56) References Cited

U.S. PATENT DOCUMENTS

| | | | |
|---|---|---|---|
| Re. 28,405 | * 5/1975 | Sollerud | ............................ 604/289 |
| 4,000,742 | 1/1977 | DiGiacomo . | |
| 4,623,095 | 11/1986 | Pronk . | |
| 4,901,765 | 2/1990 | Poe . | |
| 4,911,704 | 3/1990 | Dixon . | |
| 5,267,981 | 12/1993 | Ducoin et al. . | |
| 5,305,476 | 4/1994 | Ohyama et al. . | |
| 5,419,772 | * 5/1995 | Teitz et al. | ............................ 604/141 |
| 5,447,504 | * 9/1995 | Baker et al. | ............................ 604/289 |
| 5,468,234 | * 11/1995 | Griffin et al. | ........................ 604/290 |
| 5,549,822 | 8/1996 | Ferguson . | |
| 5,795,471 | 8/1998 | Naito . | |
| 5,843,052 | * 12/1998 | Benja-athon | ........................ 604/289 |
| 5,848,998 | * 12/1998 | Marasco, Jr. | ........................ 604/290 |
| 5,941,859 | * 8/1999 | Lerman | ............................. 604/289 |

* cited by examiner

Primary Examiner—John G. Weiss
Assistant Examiner—David J. Cho
(74) Attorney, Agent, or Firm—Michael I. Kroll

(57) ABSTRACT

Apparatus for irrigating wounds in which a housing contains a water filter and an anti-biotic, connected between a water supply and a hand spray unit, with the housing containing a hand operated valve for directing the water from the water supply through either the anti-biotic and filter or directly to the hand spray unit. A water temperature display is also included in the housing.

11 Claims, 8 Drawing Sheets

WOUND IRRIGATION SYSTEM

BACKGROUND OF THE INVENTION

1. Field of the Invention

The present invention relates generally to shower head devices and, more specifically, to a shower head assembly connected to a hand held member by a length of flexible conduit wherein the water supply can be selectively channeled either directly to the hand held unit or into a treatment housing for further processing before going to the hand held unit. The treatment housing contains an antibiotic chamber, filter media and a filter media screen whereby all particulate matter according to the filter media will be retained within said filter media and an amount of antibiotic will be released into the water being controllably ejected through the hand held unit. In addition the shower head assembly has means for measuring and displaying the temperature of the water thereby allowing control of the solution temperature.

Further the hand held unit has a trigger for selectively releasing the rotational member for varying the intensity and pattern of the water.

2. Description of the Prior Art

There are other shower devices designed to remove particles from a water supply. Typical of these is U.S. Pat. No. 5,795,471 issued to Naito on Aug. 18, 1998.

Another patent was issued to Dixon on Mar. 27, 1990 as U.S. Pat. No. 4,911,704. Yet another U.S. Pat. No. 5,549,822 was issued to Ferguson on Aug. 27, 1996 and still yet another was issued on Dec. 7, 1993 to Ducoin et al., as U.S. Pat. No. 5,267,981.

Another patent was issued to Pronk on Nov. 18, 1986 as U.S. Pat. No. 4,623,095. Another U.S. Pat. No. 5,305,476 was issued to Ohyama et al. on Apr. 26, 1994. Yet another U.S. Pat. No. 4,901,765 was issued to Poe on Feb. 20, 1990 and still yet another was issued on Jan. 4, 1997 to DiGlacomo as U.S. Pat. No. 4,000,742.

U.S. Pat. No. 5,795,471 Inventor: Harusuke Naito Issued: Aug. 18, 1998

A shower device having a water purifying function includes a cartridge type filter formed with a water inlet at one end and a water outlet at the other end and means for showering such a shower head connected to the water outlet of the cartridge type filter. The cartridge type filter contains a tannin layer consisting of a material comprising tannin, a bakuhanseki layer consisting of granular ceramic formed in a layer, a magnetite layer consisting of broken pieces of magnetite formed in a layer and provided at least on the water inlet side of the ceramic layer, and magnetizing means such as magnets for magnetizing the magnetite layer.

U.S. Pat. No. 4,911,704 Inventor: Wilbur Dixon Issued: Mar. 27, 1990

Apparatus attached to a shower head for cleansing parts of the body with a stream of medicated liquid. The apparatus includes a control valve assembly between the water supply pipe and the shower head and a flexible hose having one end connected to the control valve. The other end of the flexible tube lies within an elongated cylindrical mixing chamber with a small hole in the tube spaced from the end of the tube also lying with the mixing chamber. The forward end of the cylindrical mixing chamber is sealed by the swiveable ball-shaped end of a dispensing nozzle from which a mixture of water and medicant is discharged.

U.S. Pat. No. 5,549,822 Inventor: George E. Ferguson Issued: Aug. 27, 1996

The water purification filter is coupled intermediate any conventional shower head feed pipe and shower head. The filtration device is toroidal with a serpentine flow path. The filtration device envelopes the feed pipe which enables the shower head to remain within substantially the same location as before the insertion of the filter. To purify the shower water, the filter contains a filter media coupled between two filter screens.

U.S. Pat. No. 5,267,981 Inventor: Jacques Ducoin Issued: Dec. 7, 1993

A hygiene and treatment device wherein it comprises a pipe having a chamber at one of its ends, suitable for being put into communication with an end piece connected to a supply of water under pressure, the other end of the pipe being curved and having a longitudinal slot. The invention is particularly suitable for anal and gynecological hygiene.

U.S. Pat. No. 4,623,095 Inventor: Frank E. Pronk Issued: Nov. 18, 1986

A device to air entrain and add liquid soap or some other liquid to the water stream which flows through a shower head. There is a secondary liquid additive passageway leading into a constructed reduced pressure area of the main flow passageway of the shower water. There is a container rotatably mounted in a manner to either shut off flow of the liquid soap or other liquid, or to selectively meter the flow into the main water stream by selectively aligning aspirating air holes with an aspirating air passageway that leads into the secondary passageway.

U.S. Pat. No. 5,305,476 Inventor: Kelichi Ohyama Issued: Apr. 26, 1994

A shower bathing device comprising a passage through which hot water is passed, a chamber filled with a medical solution to supply the medical solution into the passage, a stream pump for mixing the medical solution in the chamber with hot water passing through the passage, and a screw inserted into a through hole for adjusting the amount of medical solution supplied to the stream pump, wherein hot water can be showered while including a desired density of medicine therein.

U.S. Pat. No. 4,901,765 Inventor: Frank C. Poe Issued: Feb. 20, 1990

A coupling for being mounted between the threaded end of the arm of a shower through which water flows and the shower head for mixing liquid into shower water. The coupling includes a coupling body having an inlet portion and an outlet portion with a flow path defined therebetween. A mixing chamber is mounted in fluid communication with the flow path through the coupling body which serves to selectively mix liquid such as body lotion with the water. In this regard, a vacuum generated by a venturi serves to draw the liquid into the mixing chamber. The vacuum is selectively controlled by a vacuum actuator which holds the vacuum until the shower is shut off.

U.S. Pat. No. 4,000,742 Inventor: Edward F. DiGiacomo Issued: Jan. 4, 1977

A hygiene device having a plate that is adapted to be mounted on a wall and the like with fittings thereon connected to a source of hot and cold water with a valve for adjusting the amount of hot water to be mixed with the cold water; the mixture then flowing through a fitting mounted on the plate having a slide valve that is normally closed but is opened upon inserting a quick coupler device therein. The quick coupler is provided with a receptacle for containing a medicine and a venturi into which the medicine is permitted to mix with the water that is then discharged through a douche nozzle.

While these shower head devices may be suitable for the purposes for which they were designed, they would not be as suitable for the purposes of the present invention, as hereinafter described.

SUMMARY OF THE PRESENT INVENTION

The present invention discloses a device for irrigating wounds which can be attached to a sink, tub, or shower stall. The device has means for directing the water flow through a flexible hose directly to a hand held unit for washing the wound or alternatively the water can be directed through an antibiotic treatment unit wherein the water is filtered and disinfected, further the unit has means for measuring and displaying the temperature of the water prior to transmission of the water through the hand held unit and application to the wound. The hand held unit is equipped with means for pulsing the water and for heating the water prior to application to the wound. An alternative embodiment is also provided wherein a portable enclosure is provided wherein the user can connect the present invention to a water supply such as a lavatory and therein wash a wound.

A primary object of the present invention is to provide a wound irrigation system which can be used for outpatient treatment.

Another object of the present invention is to provide a shower head attachment having the ability to selectively filter tap water and add an amount of antibiotic to said water.

Yet another object of the present invention is to provide a shower head attachment having the ability to selectively filter tap water and add an amount of antibiotic to said water before conducting said water to a hand held unit for release.

Yet another object of the present invention is to provide a shower head attachment having the ability to selectively filter tap water, add an amount of antibiotic to said water, measure the temperature of the water and display the temperature before conducting said water to a hand held unit having a trigger for selective releasing said water through an adjustable nozzle allowing a variety of patterns and water pressures during wound irrigation.

Additional objects of the present invention will appear as the description proceeds.

The present invention overcomes the shortcomings of the prior art by providing a shower head assembly connected to a hand held member by a length of flexible conduit wherein the water supply can be selectively channeled either directly to the hand held unit or into a treatment housing for further processing before going to the hand held unit. The treatment housing contains an antibiotic chamber, filter media and a filter media screen whereby all particulate matter according to the filter media will be retained within said filter media and an amount of antibiotic will be released into the water being controllably ejected through the hand held unit.

Further the shower head assembly having means for measuring and displaying the temperature of the water thereby allowing control of the solution temperature.

The foregoing and other objects and advantages will appear from the description to follow. In the description reference is made to the accompanying drawings, which form a part hereof, and in which is shown by way of illustration specific embodiments in which the invention may be practiced. These embodiments will be described in sufficient detail to enable those skilled in the art to practice the invention, and it is to be understood that other embodiments may be utilized and that structural changes may be made without departing from the scope of the invention. In the accompanying drawings, like reference characters designate the same or similar parts throughout the several views.

The following detailed description is, therefore, not to be taken in a limiting sense, and the scope of the present invention is best defined by the appended claims.

BRIEF DESCRIPTION OF THE DRAWINGS

In order that the invention may be more fully understood, it will now be described, by way of example, with reference to the accompanying drawings in which.

DESCRIPTION OF THE PREFERRED EMBODIMENT(S)

Turning now descriptively to the drawings, in which similar reference characters denote similar elements throughout the several views, FIGS. 1 through 10 illustrate the present invention being a device for irrigating wounds.

Figure 1:
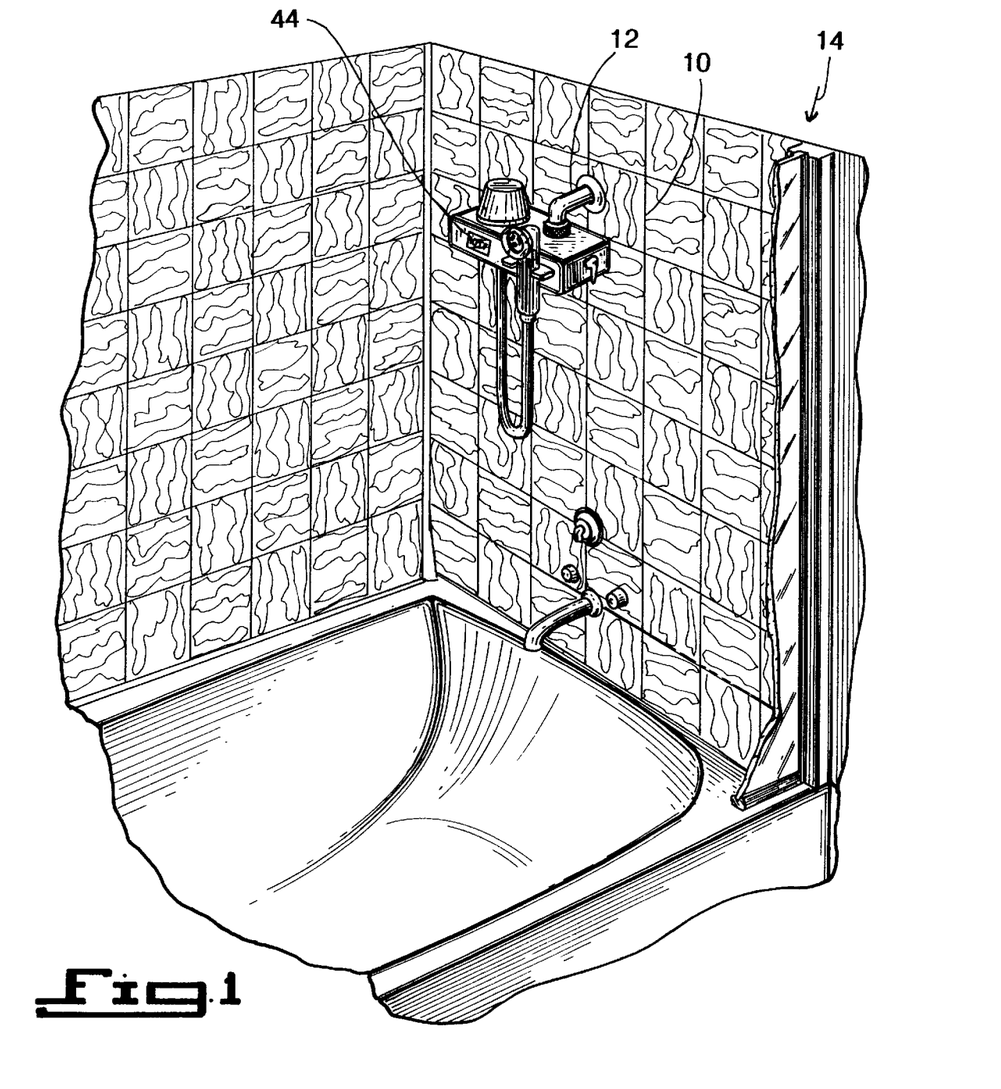
FIG. 1 is a perspective view of the wound irrigation system of the present invention mounted to a shower fixture.

Turning to FIG. 1, therein is shown a perspective view of the wound irrigation system 10 mounted to a shower fixture 12 which serves as the required water supply and is within a shower stall 14 which will capture the runoff from washing the wound with the present invention.

Figure 2:
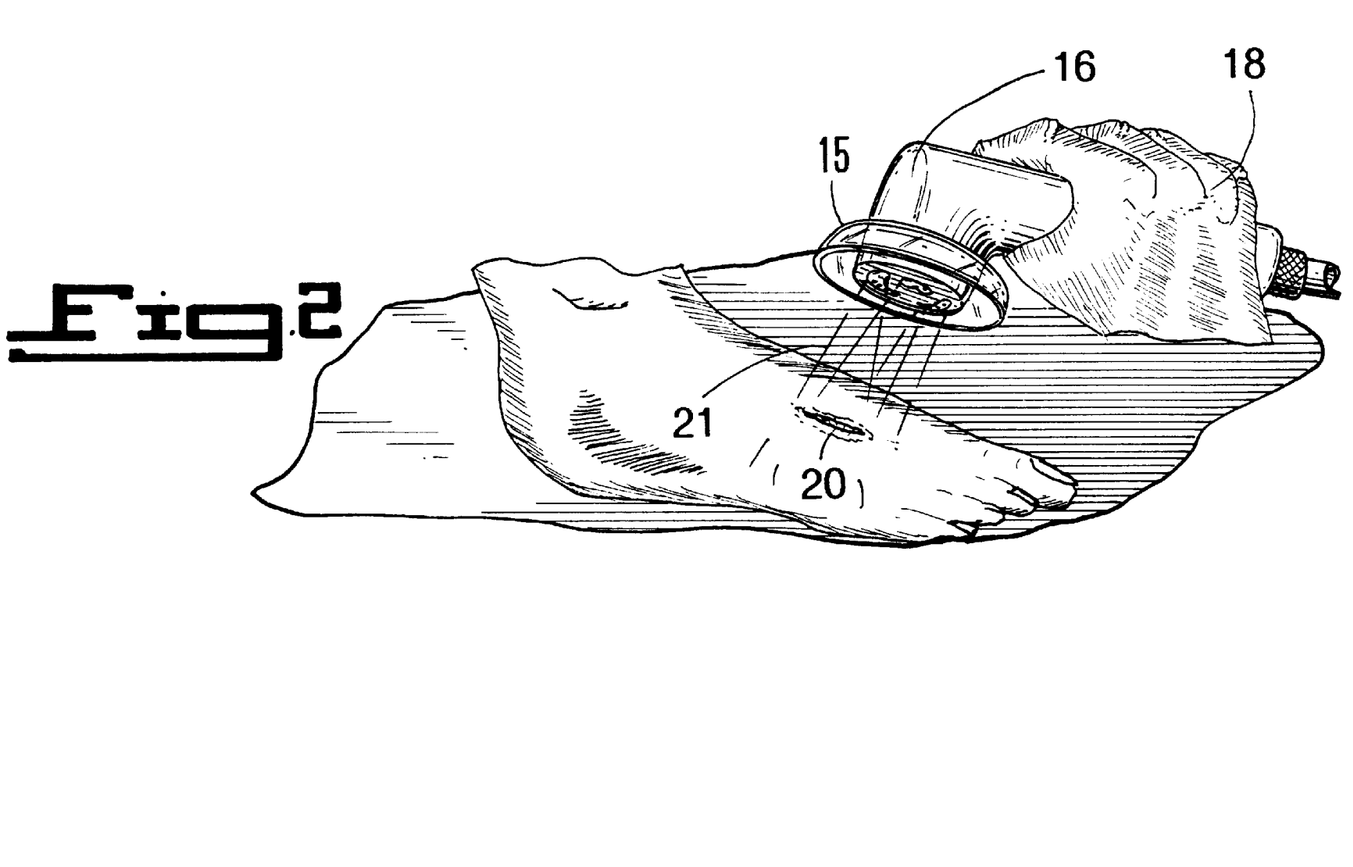
FIG. 2 is a perspective view of the hand piece of the wound irrigation system being utilized to irrigate a foot wound.

Turning to FIG. 2, therein is shown a perspective view of the hand piece 16 of the wound irrigation system being utilized by a user 18 to irrigate a foot wound 20. Shown is the hand piece 16 spraying a stream of water 21 onto the foot wound 20.

Figure 3:
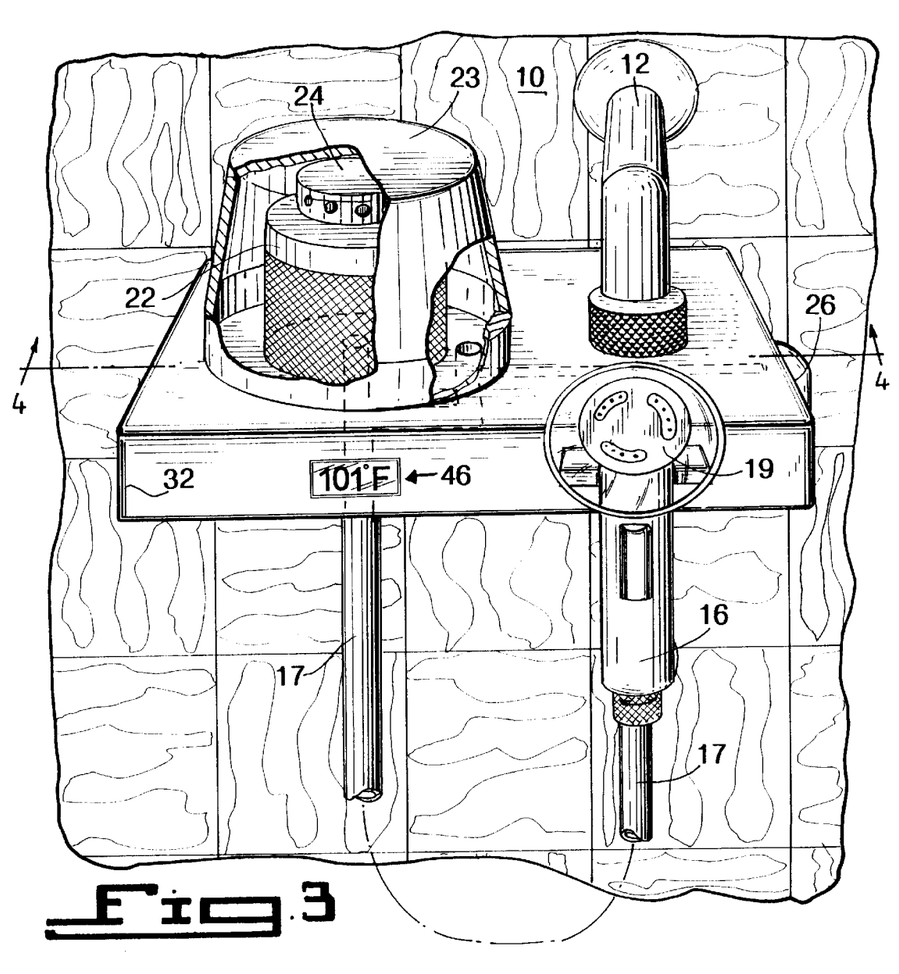
FIG. 3 is a front perspective view of the wound irrigation device of the present invention with parts broken away to show the filter 22 and antibiotic chamber 24 and solution indicator 46 and hand held shower head as well as the flow diverter handle control.

Turning to FIG. 3, therein is shown a front perspective view of the wound irrigation device of the present invention 10 with parts broken away to show the filter housing 23, filter 22 and an antibiotic chamber 24, temperature indicator 46, and a hand held unit 16 and shower head 19 as well as the flow diverter handle 26 along with the hand piece 16, housing 32, and flexible line 17 connecting the water line to the hand piece 16. Spray shield 15 is affixed to hand piece 16.

Figure 4:
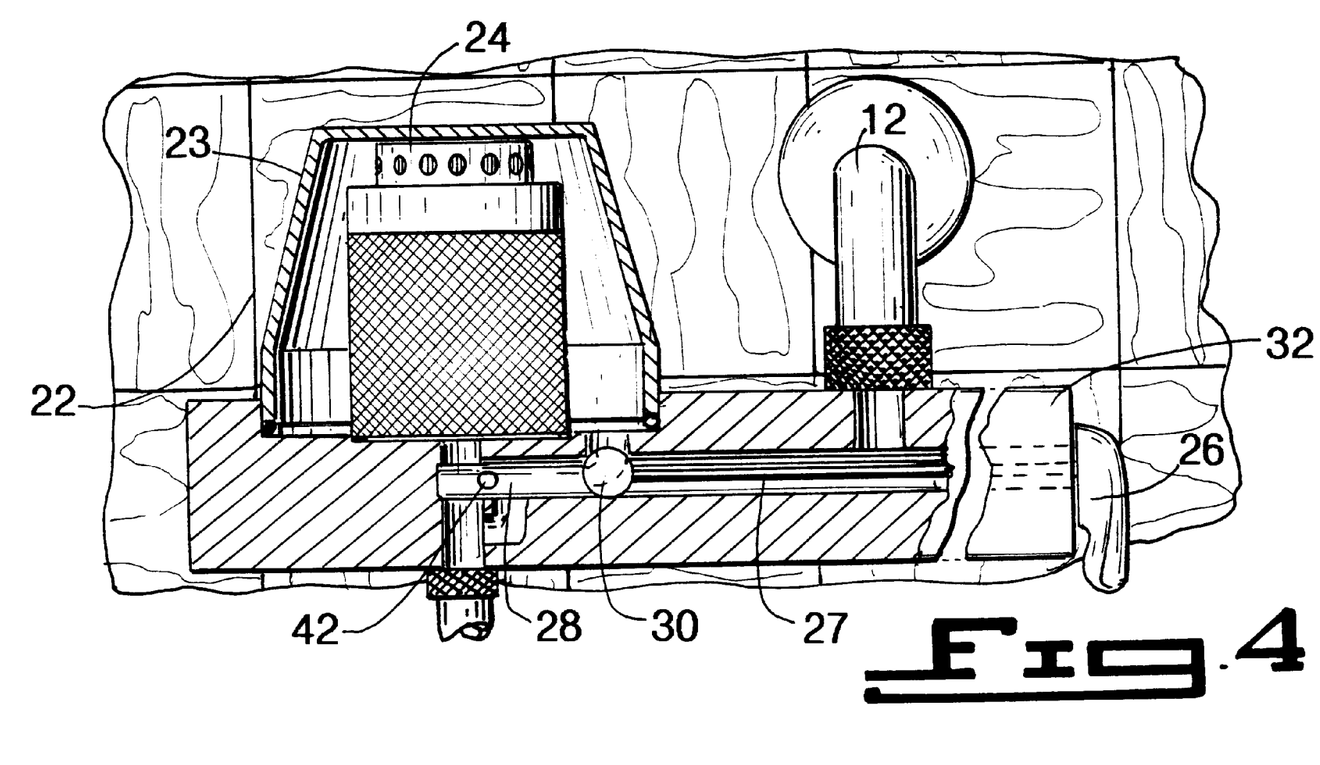
FIG. 4 is a sectional view taken generally on line 4 of FIG. 3.

Turning to FIG. 4, therein is shown a sectional view taken generally on line 4 of FIG. 3 as indicated. Shown therein is a shower fixture being a water fixture 12 furnishing the source of water along with the filter 22 housing 23 and the antibiotic chamber 24. Also shown are interconnecting pipes or conduits 28 for the water flow required by the present invention 10. Also shown is a control handle 26, control shaft 27, and control valve 30 of the standard type which directs water flow either directly to the hand piece 16 or through the filter unit 22 and thereafter to the hand piece 16. The control handle 26 directs water either toward the hand held unit 16 or toward the treatment unit 24.

Figures 5, 6:
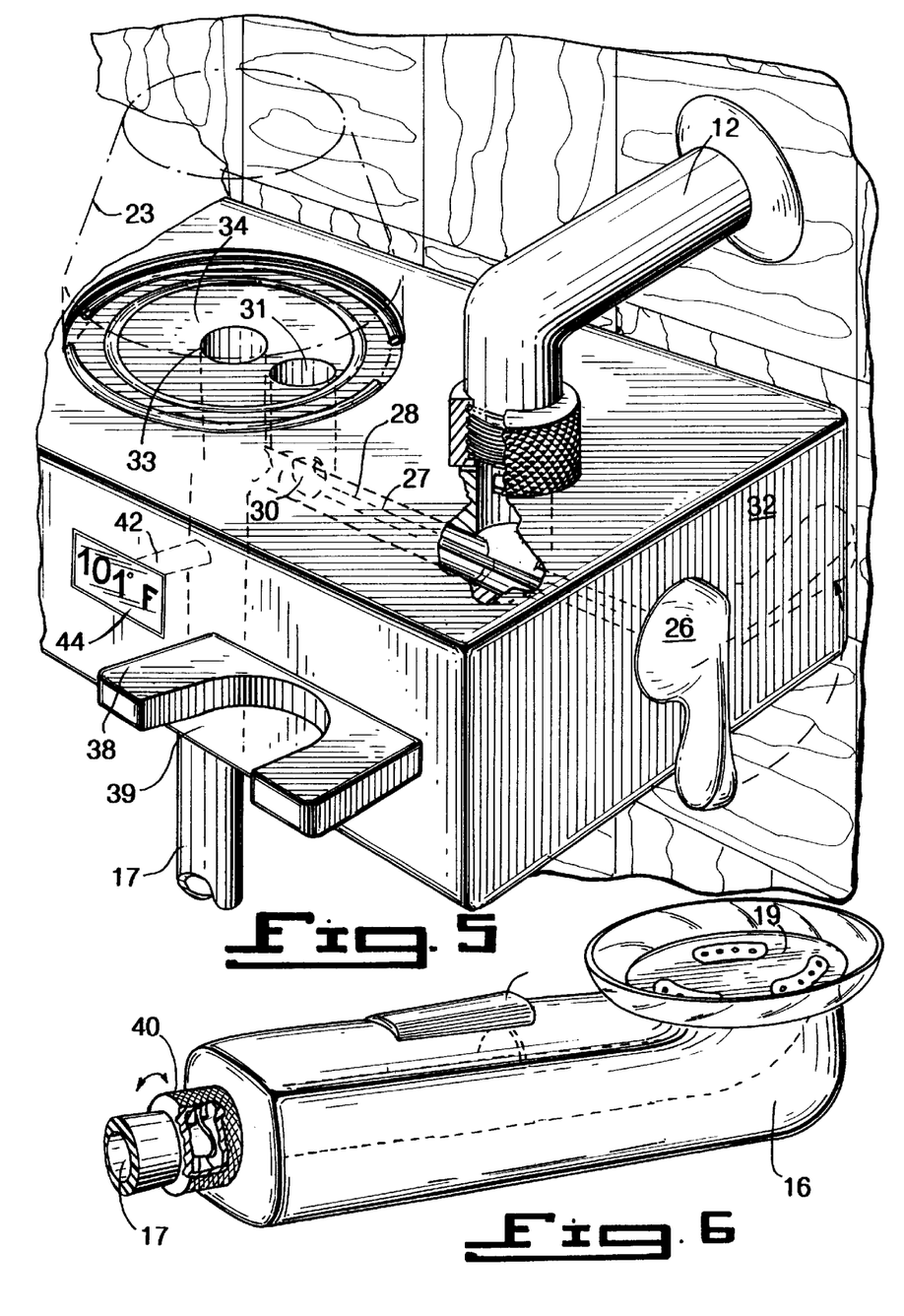
FIG. 5 is an enlarged perspective view showing a portion of the wound irrigation device showing the temperature sensor 42 and temperature display 44 with the filter and housing remover.
FIG. 6 is a perspective view of the hand held shower showing the location of a pulse control valve and flow control handle.

Turning to FIG. 5, therein is shown an enlarged perspective view of the present invention 10 showing a portion of the wound irrigation device without the filter and filter housing. Shown therein is the water supply of the shower fixture 12 along with a housing 32, the control handle 26 and a recessed base receiving and connecting means 34 for receiving the filter housing 23 contained on the base or housing 32 which holds the filter housing unit 23 onto the base 32. Also shown are temperature sensor 42, temperature display 44, conduits 28 and control valve 30 which directs water to the hand held unit 16 or to the antibiotic treatment housing 23. Also shown is a receptacle 38 having a cradle 39 therein for holding the hand held unit 16 onto the housing 32. Conduit 31 is the inlet conduit which allows water to enter the filter housing 23 when the control handle 26 is set on that selectable position and conduit 33 thereafter allows water to exit housing 23 and travel through flexible line 17 into the hand piece (not shown).

Turning to FIG. 6, therein is shown a perspective view of the hand held shower unit 16 with shower head 19 and inlet line 17 showing the location of the pulse control valve 40 and a flow control trigger 54 which a user can operate with a finger of his hand while holding the unit 16.

Figure 7:
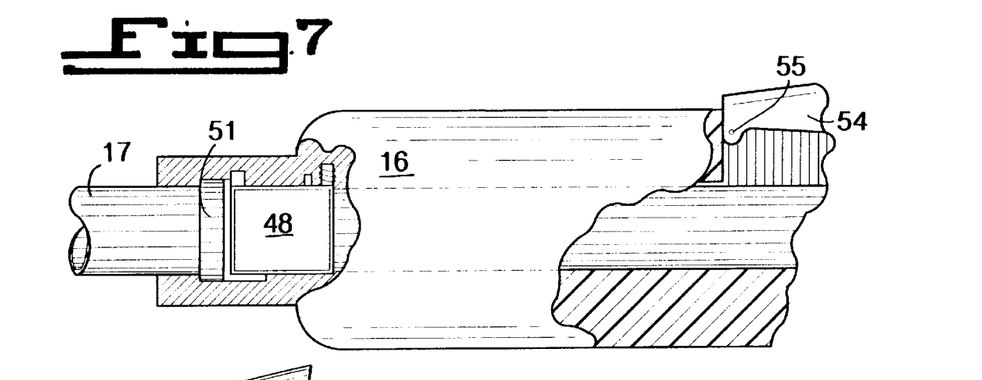
FIG. 7 is a side elevation of part of the hand held shower head showing the pulse control vane.

Turning to FIG. 7, therein is shown a side elevation view of the part of the hand held unit 16 showing the pulse control vane 48. Also shown are the inlet line 17 with handle connecting means 51 and trigger 54 with hinges 55.

Figures 8, 9:
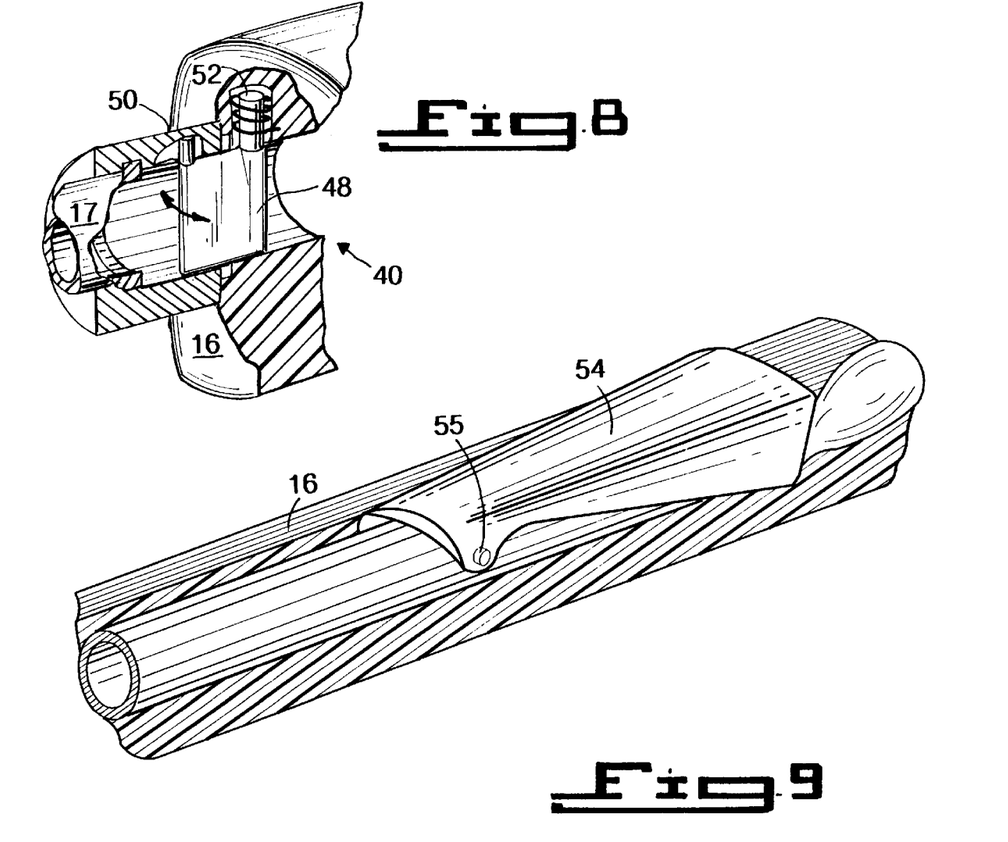
FIG. 8 is a perspective view in section showing details of the water pulsing vane and control cam for adjusting same in the pulse center ring.
FIG. 9 is an enlarged perspective showing the details of the water flow control trigger.

Turning to FIG. 8, therein is shown a perspective view in section showing details of the water pulsing vane showing the control vane 48 and control cam 50 for adjusting the water pulse and the pulse center ring. Also shown is the spring loaded movably mounted shaft means 52 allowing the vane to rapidly oscillate from side to side so as to cause the water to pulse in the standard manner.

Turning to FIG. 9, therein is shown an enlarged perspective view of the present invention 10 showing a shower hand piece 16, as well as details of the water flow control trigger 54 with hinge 55 of the standard type.

Figure 10:
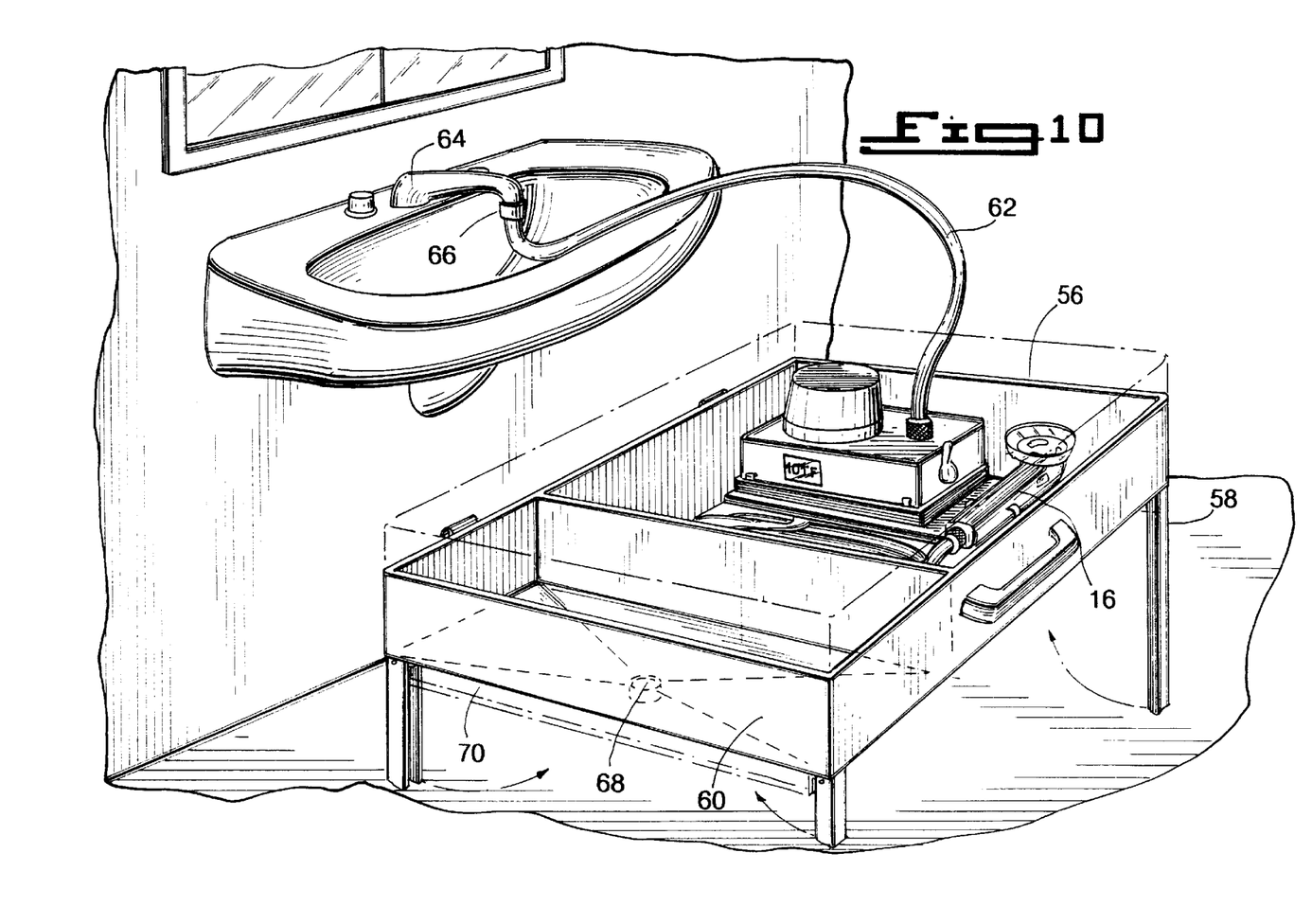
FIG. 10 is an alternate embodiment situated in a transportable self-contained suitcase like arrangement having retractable legs and built-in catch basin.
Figure 11:
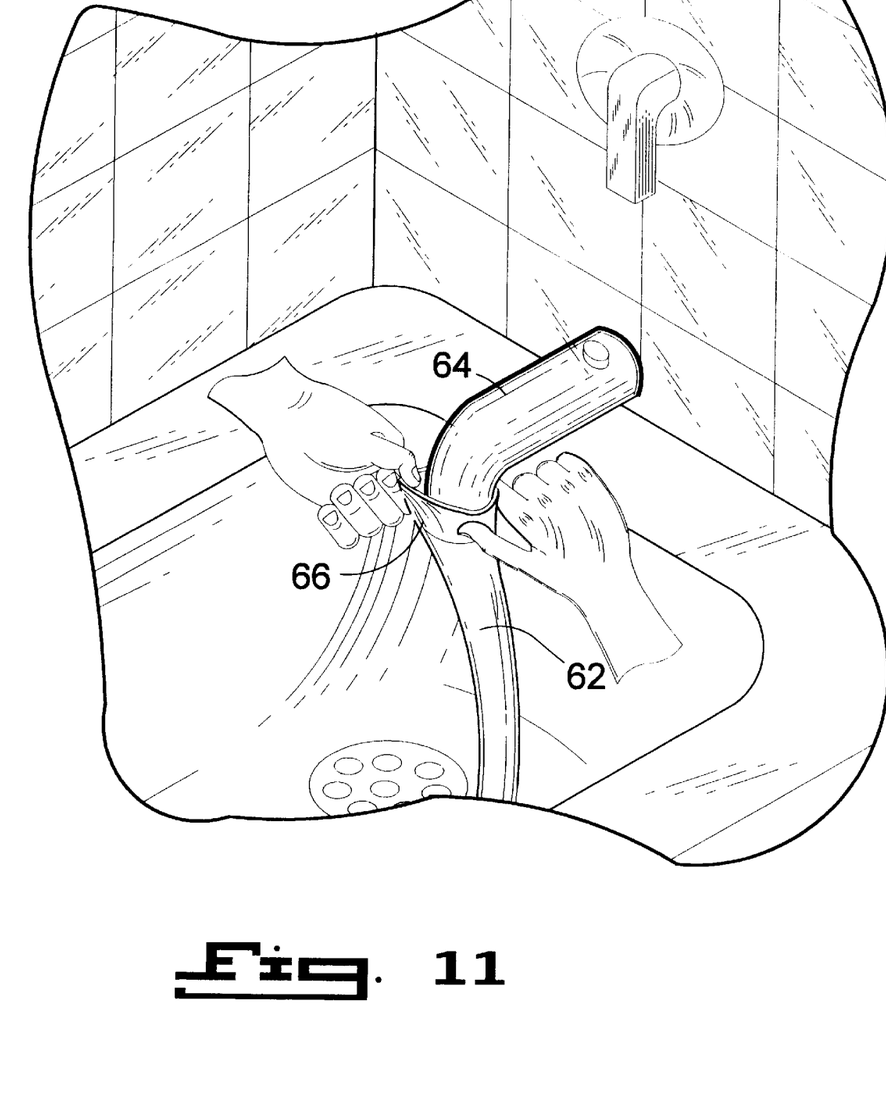
FIG. 11 is a perspective view of one distal end of the connection means of the alternate embodiment showing an elastomeric member being attached over a tub spigot.

Turning to FIG. 10, therein is shown an alternative embodiment situated in a transportable self-contained suitcase-like enclosure 56 or like arrangement having retractable legs 58 and having a built-in catch basin 60. Also shown is a water supply hose 62 and water supply faucet or nozzle 64 having connecting means 66 for attaching the hose 62 to the faucet 64. The apparatus of FIG. 10 functions in all respects as the apparatus shown throughout this specification other than the fact that it is portable as shown in FIG. 10 and has a different means 67 for connecting the water supply to the present invention 10. In operation the apparatus of the alternative embodiment of FIG. 10 is operated by the user placing a body part in the catch basin 60 whereby the user would then use the hand piece 16 to flush his wound and thereafter, the catch basin would be emptied into a lavatory or through the drain plug 68 provided in the catch basin 60. Note that the legs 58 are retractable and the folded position of the legs 70 is also shown.

What is claimed to be new and desired to be protected by Letters Patent is set forth in the claims:

1. An apparatus for irrigating wounds, comprising:

a) a hand held spray unit for spraying a wound;

b) a first housing containing first means for hydraulically connecting said hand held spray unit to a water supply;

c) an antibiotic treatment unit and a water filter enclosed in a second, removable housing mounted on top of said first housing for disinfecting and filtering said water supply;

d) a second means within said first housing for hydraulically connecting said antibiotic treatment unit and said water filter to said water supply and said hand held spray unit;

e) a temperature sensor within said first housing for measuring the temperature of the water leaving said first housing for delivery to said hand held spray;

f) a temperature display on the outside of said first housing for displaying the aforesaid temperature of the water leaving said first housing being delivered to said hand held spray;

g) means in said first housing for selectively directing the flow of water to said hand spray unit through either into said second housing for flow through said antibiotic treatment unit and said water filter or directly to said hand spray unit bypassing said antibiotic unit and water filter; and, h) said directing means comprising a handle on the outside of said first housing, a valve within said first housing for directing the water flow, and means connecting said handle to said valve for selecting the path of the water flow within said first housing.

2. The apparatus of claim 1, wherein said first means for hydraulically connecting said hand held spray unit to a water supply further comprises flexible connection means.

3. The apparatus of claim 1, said hand held spray unit further comprises means for pulsing said water spray.

4. The apparatus of claim 3, said means for pulsing further comprises a vane in said hand held control unit.

5. The apparatus of claim 3, said means for pulsing further comprises a pulsing vane and control cam in said hand held control unit.

6. The apparatus of claim 4, said pulsing vane further comprising a spring loaded shaft upon which said vane oscillates.

7. The apparatus of claim 1, wherein said housing further comprises a portable suitcase-like enclosure having retractable legs thereon.

8. The apparatus of claim 7, said portable enclosure further comprises means for connection to a water supply, said portable enclosure further comprises a catch basin having a drain plug therein.

9. The apparatus of claim 1, said hand held spray unit further comprises a trigger for operation by a finger of the hand of the user holding said spray unit.

10. The apparatus of claim 1, said hand held spray unit further comprising a spray shield.

11. The apparatus of claim 1 in which the water supply is connected to a top surface of said first housing adjacent said second housing.

* * * * *